(12) United States Patent
Kralicky et al.

(10) Patent No.: US 11,744,658 B2
(45) Date of Patent: *Sep. 5, 2023

(54) ALIGNMENT DIFFERENCE SAFETY IN A MASTER-SLAVE ROBOTIC SYSTEM

(71) Applicant: Titan Medical Inc., Toronto (CA)

(72) Inventors: Joseph Kralicky, North Kingston, RI (US); Peter Cameron, Menlo Park, CA (US); Rene Robert, East Greenwich, RI (US)

(73) Assignee: TITAN MEDICAL INC., Toronto (CA)

( * ) Notice: Subject to any disclaimer, the term of this patent is extended or adjusted under 35 U.S.C. 154(b) by 83 days.

This patent is subject to a terminal disclaimer.

(21) Appl. No.: 17/458,989

(22) Filed: Aug. 27, 2021

(65) Prior Publication Data
US 2022/0047340 A1 Feb. 17, 2022

Related U.S. Application Data

(63) Continuation of application No. 16/176,221, filed on Oct. 31, 2018, now Pat. No. 11,103,318, which is a
(Continued)

(51) Int. Cl.
*A61B 34/30* (2016.01)
*A61B 34/35* (2016.01)
(Continued)

(52) U.S. Cl.
CPC .............. *A61B 34/30* (2016.02); *A61B 34/35* (2016.02); *A61B 34/37* (2016.02); *A61B 34/70* (2016.02);
(Continued)

(58) Field of Classification Search
CPC ......... A61B 34/30; A61B 34/35; A61B 34/37; A61B 34/70; A61B 34/71; A61B 34/74;
(Continued)

(56) References Cited

U.S. PATENT DOCUMENTS 8,027,714 B2   9/2011   Shachar
8,332,072 B1   12/2012  Schaible et al.
(Continued)

FOREIGN PATENT DOCUMENTS

CA    2 816 888       5/2012
WO    WO 2014/151621 A1   9/2014

OTHER PUBLICATIONS

Extended European Search report received in Application No. 16734868.9, dated Apr. 13, 2018.
(Continued)

*Primary Examiner* — Robert T Nguyen
(74) *Attorney, Agent, or Firm* — Knobbe, Martens, Olson & Bear LLP

(57) ABSTRACT

A method of operating a robotic control system comprising a master apparatus in communication with an input device having a handle and a slave system having a tool having an end effector whose position and orientation is determined in response to a position and orientation of the handle. The method involves producing a desired end effector position and a desired end effector orientation of the end effector, in response to a current position and a current orientation of the handle. The method further involves causing the input device to provide haptic feedback that impedes translational movement of the handle, while permitting rotational movement of the handle and preventing movement of the end effector, when a rotational alignment difference between the handle and the end effector meets a first criterion. The method further involves re-enabling translational movement of the handle when the rotational alignment difference meets a second criterion.

19 Claims, 11 Drawing Sheets

Related U.S. Application Data continuation of application No. 15/542,398, filed as application No. PCT/CA2016/000007 on Jan. 8, 2016, now Pat. No. 10,159,536.

(60) Provisional application No. 62/101,804, filed on Jan. 9, 2015.

(51) Int. Cl.

| | |
|---|---|
| *B25J 9/16* | (2006.01) |
| *A61B 34/00* | (2016.01) |
| *A61B 34/37* | (2016.01) |
| *A61B 90/00* | (2016.01) |
| *B25J 3/04* | (2006.01) |
| *B25J 13/02* | (2006.01) |
| *B25J 19/06* | (2006.01) |
| *B25J 13/06* | (2006.01) |

(52) U.S. Cl.
CPC ............ *A61B 34/71* (2016.02); *A61B 34/74* (2016.02); *A61B 34/76* (2016.02); *A61B 34/77* (2016.02); *A61B 90/03* (2016.02); *B25J 3/04* (2013.01); *B25J 9/1674* (2013.01); *B25J 9/1689* (2013.01); *B25J 13/025* (2013.01); *B25J 13/065* (2013.01); *B25J 19/06* (2013.01); *A61B 2034/302* (2016.02); *A61B 2034/742* (2016.02); *G05B 2219/35419* (2013.01); *G05B 2219/36422* (2013.01); *G05B 2219/39439* (2013.01); *G05B 2219/40144* (2013.01); *G05B 2219/45117* (2013.01); *G05B 2219/45118* (2013.01)

(58) Field of Classification Search
CPC ......... A61B 34/76; A61B 34/77; A61B 90/03; A61B 2034/302; A61B 2034/742; B25J 3/04; B25J 9/1674; B25J 9/1689; B25J 13/025; B25J 13/065; B25J 19/06; B25J 9/1692; G05B 2219/35419; G05B 2219/36422; G05B 2219/39439; G05B 2219/40144; G05B 2219/45117; G05B 2219/45118

See application file for complete search history.

(56) References Cited

U.S. PATENT DOCUMENTS

| | | | |
|---|---|---|---|
| 9,161,803 B2 | 10/2015 | Yates et al. | |
| 10,159,536 B2 * | 12/2018 | Kralicky | B25J 13/065 |
| 10,524,871 B2 | 1/2020 | Liao | |
| 11,103,318 B2 * | 8/2021 | Kralicky | B25J 3/04 |
| 2002/0082612 A1 | 6/2002 | Moll et al. | |
| 2010/0082039 A1* | 4/2010 | Mohr | B25J 9/1692 |
| | | | 700/83 |
| 2010/0332031 A1 | 12/2010 | Itkowitz et al. | |
| 2012/0150349 A1 | 6/2012 | Rust et al. | |
| 2014/0180290 A1 | 6/2014 | Otto et al. | |
| 2014/0216192 A1 | 8/2014 | Dize et al. | |
| 2015/0025549 A1 | 1/2015 | Kilroy et al. | |
| 2015/0038981 A1 | 2/2015 | Kilroy et al. | |
| 2015/0038982 A1 | 2/2015 | Kilroy et al. | |
| 2015/0150635 A1 | 6/2015 | Kilroy et al. | |
| 2015/0157410 A1 | 6/2015 | Kilroy et al. | |
| 2015/0209965 A1 | 7/2015 | Kilroy et al. | |
| 2016/0058461 A1 | 3/2016 | Ravikumar et al. | |
| 2016/0199984 A1 | 7/2016 | Lohmeier et al. | |
| 2016/0303739 A1 * | 10/2016 | Apkarian | H04L 67/303 |
| 2017/0035526 A1 | 2/2017 | Farritor et al. | |
| 2017/0209217 A1 | 7/2017 | Jensen | |
| 2017/0333139 A1 | 11/2017 | Suresh et al. | |
| 2018/0046062 A1 | 2/2018 | Fisher et al. | |
| 2018/0078321 A1 | 3/2018 | Liao | |
| 2018/0271607 A1* | 9/2018 | Kralicky | B25J 3/04 |
| 2019/0201147 A1 | 7/2019 | Kralicky et al. | |
| 2020/0179068 A1* | 6/2020 | Peine | A61B 34/35 |
| 2021/0008660 A1 | 1/2021 | Limanov et al. | |

OTHER PUBLICATIONS

International Search Report for International Application No. PCT/CA2016/000007 dated Mar. 17, 2016 in 4 pages.
Written Opinion for International Application No. PCT/CA2016/000007 dated Mar. 17, 2016 in 5 pages.

* cited by examiner

Compute the offset angle between the master and the slave z-axes $$\phi_{EE\_TO\_MASTER} = \mathrm{acos}\,(R_{EENEW}(1,3) * R_{MCURR}(1,3) + R_{EENEW}(2,3) * R_{MCURR}(2,3) + R_{EENEW}(3,3) * R_{MCURR}(3,3))$$

ALIGNMENT DIFFERENCE SAFETY IN A MASTER-SLAVE ROBOTIC SYSTEM

INCORPORATION BY REFERENCE

This application is a continuation of U.S. patent application Ser. No. 16/176,221, filed on Oct. 31, 2018, and issued as U.S. Pat. No. 11,103,318 on Aug. 31, 2021, which is a continuation of U.S. patent application Ser. No. 15/542,398, filed on Jul. 7, 2017, and issued as U.S. Pat. No. 10,159,536 on Dec. 25, 2018, which is a U.S. national phase of International Patent Application No. PCT/CA2016/000007, filed on Jan. 8, 2016, which claims priority to U.S. Provisional Patent Application No. 62/101,804, filed on Jan. 9, 2015, each of which is hereby incorporated by reference herein in their entireties.

BACKGROUND OF THE INVENTION

1. Field of Invention

This invention relates to master-slave robotic systems such as those used for laparoscopic surgery and more particularly to prevention of operator control of the surgical tools when an alignment difference between the master and slave exceeds a threshold value.

2. Description of Related Art

In a robotic system that allows for clutching of an end effector wherein movement of the end effector in response to movement of a handle can be selectively interrupted by the clutch mechanism such that the handle can be moved and rotated while the position and rotation of the end effector is held stationary, there is a possibility that the orientation of the handle and the orientation of the end effector will come out of rotational alignment. Should this occur, the commanded end effector orientation can differ significantly from the handle orientation. When the alignment difference is large, movement of the slave instrument may not feel as though it is fundamentally linked to the motion of the master handle, from the user's perspective.

SUMMARY OF THE INVENTION

The disclosure describes a method of operating a robotic control system comprising a master apparatus in communication with an input device having a handle capable of translational and rotational movement and a slave system having a tool positioning device holding a tool having an end effector whose position and orientation is determined in response to a position and orientation of the handle. The method involves producing a desired end effector position and a desired end effector orientation of the end effector, in response to a current position and a current orientation of the handle. The method further involves causing the input device to provide haptic feedback that impedes translational movement of the handle, while permitting rotational movement of the handle and while disabling translational and rotational movement of the end effector, when a rotational alignment difference between the handle and the end effector meets a disablement criterion. The method further involves enabling translational movement of the handle when the rotational alignment difference meets an enablement criterion.

Producing the desired end effector position and desired end effector orientation may include causing the master apparatus to receive current handle position signals ($\bar{P}_{MCURR}$) and current handle orientation signals ($R_{MCURR}$) representing a current position and a current orientation respectively of the handle of the input device, and causing the master apparatus to produce new end effector position signals ($\bar{P}_{EENEW}$) and new end effector orientation signals ($R_{EENEW}$) defining the desired end effector position and the desired end effector orientation, respectively of the end effector, in response to the current handle position signals ($\bar{P}_{MCURR}$) and the current handle orientation signals ($R_{MCURR}$).

Causing the master apparatus to receive the current handle position signals and the current handle orientation signals may involve causing the master apparatus to periodically receive the current handle position signals and the current handle orientation signals.

The method may further involve causing the master apparatus to determine the rotational alignment difference between the handle and the end effector in response to the current handle orientation signals ($R_{MCURR}$) and the new end effector orientation signals ($R_{EENEW}$).

Causing the master apparatus to determine a rotational alignment difference between the handle and the end effector may involve causing the master apparatus to determine an angle through which the end effector would have to be rotated to align it with the current handle orientation.

Causing the master apparatus to determine a rotational alignment difference between the handle and the end effector may further involve determining whether the angle of rotation is less than a threshold.

Causing the input device to provide haptic feedback may involve causing the master apparatus to transmit a haptic feedback signal to the input device to cause the input device to provide the haptic feedback that impedes the translational movement of the handle.

Enabling translational movement of the handle when the rotational alignment difference meets an enablement criterion may involve transmitting to the slave system a control signal identifying the end effector position and orientation signals based on a current position and orientation of the handle, and disabling movement of the end effector in response to any movement of the handle may involve transmitting to the slave system a control signal identifying the end effector position and orientation signals determined from a previous position and orientation of the handle.

The method may involve causing the master apparatus to receive an enablement signal.

The method may further involve generating the enablement signal such that the enablement signal selectively has an active state or an inactive state.

The method may involve causing the master apparatus to detect a change of the enablement signal from the inactive state to the active state and when the change is detected: causing the master apparatus to store the current handle position signals ($\bar{P}_{MCURR}$) and the current handle orientation signals ($R_{MCURR}$) as master base position signals ($\bar{P}_{MBASE}$) and master base rotation signals ($R_{MBASE}$) respectively, in response to the change of the enablement signal. The method may involve causing the master apparatus to store the new end effector position signals ($\bar{P}_{EENEW}$) and the new end effector orientation signals ($R_{EENEW}$) as end effector base position signals ($\bar{P}_{EEBASE}$) and end effector base rotation signals ($R_{EEBASE}$) respectively, in response to the change of the enablement signal.

Causing the master apparatus to compute the new end effector position signals ($\bar{P}_{EENEW}$) and the new end effector orientation signals ($R_{EENEW}$) may involve causing the master apparatus to compute the new end effector position signals and the new end effector orientation signals according to the following relations:

$$\bar{P}_{EENEW}=A(\bar{P}_{MCURR}-\bar{P}_{MBASE})+\bar{P}_{EEBASE}; \text{ and}$$

$$R_{EENEW}=R_{EEBASE}R_{MBASE}^{-1}R_{MCURR}.$$

The method may involve causing the control signal to be further dependent on the state of the enablement signal, such that the control signal identifies the end effector position and orientation signals based on a current position and orientation of the handle when the alignment difference is less than the disablement criterion and the enablement signal is in the active state, and the control signal identifies the end effector position and orientation signals based on a previous position and orientation of the handle when the enablement signal is in the inactive state.

The method may further involve causing the master apparatus to produce annunciation signals for causing an annunciator to annunciate an indication of a relative rotational alignment of the handle and the end effector.

Causing the master apparatus to produce annunciation signals may include causing the master apparatus to produce display control signals for causing a display to depict the relative alignment.

The disclosure describes a non-transitory computer readable medium encoded with codes for directing a processor to execute the any of the methods described above.

The disclosure further describes an apparatus for use in a robotic control system the apparatus in communication with an input device having a handle capable of translational and rotational movement and in communication with a slave system having a tool having an end effector whose position and orientation is determined in response to a position and orientation of the handle. The apparatus includes producing means for producing a desired end effector position and a desired end effector orientation of the end effector, in response to a current position and a current orientation of the handle.

The apparatus further includes causing means for causing the input device to provide haptic feedback that impedes translational movement of the handle, while causing rotational movement of the handle to be enabled and while causing translational movement of the end effector in response to translational movement of the handle to be disabled, when a rotational alignment difference between the handle and the end effector meets a disablement criterion. The apparatus further includes enabling means for enabling translational movement of the handle when the rotational alignment difference meets an enablement criterion.

The producing means may include means for receiving current handle position signals ($\bar{P}_{MCURR}$) and current handle orientation signals ($R_{MCURR}$) representing a current position and a current orientation respectively of the handle of the input device, and means for producing new end effector position signals ($\bar{P}_{EENEW}$) and new end effector orientation signals ($R_{EENEW}$) defining the desired end effector position and the desired end effector orientation, respectively of the end effector, in response to the current handle position signals ($\bar{P}_{MCURR}$) and the current handle orientation signals ($R_{MCURR}$).

The means for receiving the current handle position signals and the current handle orientation signals may include means for periodically receiving the current handle position signals and the current handle orientation signals.

The apparatus may include means for determining the rotational alignment difference between the handle and the end effector in response to the current handle orientation signals ($R_{MCURR}$) and the new end effector orientation signals ($R_{EENEW}$).

The means for determining the rotational alignment difference between the handle and the end effector may include means for determining an angle through which the end effector would have to be rotated to align it with the current handle orientation.

The apparatus may include means for determining whether the angle of rotation is less than a threshold.

Causing means may include means for transmitting a haptic feedback signal to the input device to cause the input device to provide the haptic feedback that impedes the translational movement of the handle.

The enabling means may include means for transmitting to the slave system a control signal identifying the end effector position and orientation signals based on a current position and orientation of the handle, and means for disabling movement of the end effector in response to any movement of the handle comprising means for transmitting to the slave system a control signal identifying end effector position and orientation signals determined from a previous position and orientation of the handle.

The apparatus may include means for receiving an enablement signal.

The apparatus may include means for generating the enablement signal such that the enablement signal selectively has an active state or an inactive state.

The apparatus may include means for detecting a change of the enablement signal from the inactive state to the active state, means for storing the current handle position signals ($\bar{P}_{MCURR}$) and the current handle orientation signals ($R_{MCURR}$) as master base position signals ($\bar{P}_{MBASE}$) and master base rotation signals ($R_{MBASE}$) respectively, in response to the change of the enablement signal, and means for storing the new end effector position signals ($\bar{P}_{EENEW}$) and the new end effector orientation signals ($R_{EENEW}$) as end effector base position signals ($\bar{P}_{EEBASE}$) and end effector base rotation signals ($R_{EEBASE}$) respectively, in response to the change of the enablement signal.

The means for producing the new end effector position signals ($\bar{P}_{EENEW}$) and the new end effector orientation signals ($R_{EENEW}$) may include means for computing the new end effector position signals and the new end effector orientation signals according to the following relations:

$$\bar{P}_{EENEW}=A(\bar{P}_{MCURR}-\bar{P}_{MBASE})+\bar{P}_{EEBASE}; \text{ and}$$

$$R_{EENEW}=R_{EEBASE}R_{MBASE}^{-1}R_{MCURR}.$$

The apparatus may include means for causing the control signal to be further dependent on the state of the enablement signal, such that the control signal identifies the end effector position and orientation signals based on a current position and orientation of the handle when the alignment difference is less than the disablement criterion and the enablement signal is in the active state, and the control signal identifies the end effector position and orientation based on a previous position and orientation of the handle when the enablement signal is in the inactive state.

The apparatus may include annunciation signal means for producing annunciation signals for causing an annunciator to annunciate an indication of a relative rotational alignment of the handle and the end effector.

The annunciation signal causing means may include means for producing display control signals for causing a display to depict the relative alignment.

The disclosure further describes an apparatus for use in a robotic control system, the apparatus in communication with an input device having a handle capable of translational and rotational movement and in communication with a slave system having a tool having an end effector whose position and orientation is determined in response to a position and orientation of the handle. The apparatus includes at least one processor circuit configured to produce a desired end effector position and a desired end effector orientation of the end effector, in response to a current position and a current orientation of the handle, to cause the input device to provide haptic feedback that impedes translational movement of the handle, while causing rotational movement of the handle to be enabled and while causing translational movement of the end effector in response to translational movement of the handle to be disabled, when a rotational alignment difference between the handle and the end effector meets a disablement criterion, and to enable translational movement of the handle when the rotational alignment difference meets an enablement criterion.

The at least one processor circuit may be configured to produce the desired end effector position and desired end effector orientation by receiving current handle position signals ($\bar{P}_{MCURR}$) and current handle orientation signals ($R_{MCURR}$) representing a current position and a current orientation respectively of the handle of the input device, and producing new end effector position signals ($\bar{P}_{EENEW}$) and new end effector orientation signals ($R_{EENEW}$) defining the desired end effector position and the desired end effector orientation, respectively of the end effector, in response to the current handle position signals ($\bar{P}_{MCURR}$) and the current handle orientation signals ($R_{MCURR}$).

The at least one processor circuit may be configured to receive the current handle position signals and the current handle orientation signals by periodically receiving the current handle position signals and the current handle orientation signals.

The at least one processor circuit may be further configured to determine the rotational alignment difference between the handle and the end effector in response to the current handle orientation signals ($R_{MCURR}$) and the new end effector orientation signals ($R_{EENEW}$).

The at least one processor circuit may be configured to determine a rotational alignment difference between the handle and the end effector by determining an angle through which the end effector would have to be rotated to align it with the current handle orientation.

The at least one processor circuit may be further configured to determine whether the angle of rotation is less than a threshold.

The at least one processor circuit may be configured to cause the input device to provide haptic feedback by transmitting a haptic feedback signal to the input device to cause the input device to provide the haptic feedback that impedes the translational movement of the handle.

The at least one processor circuit may be configured to enable translational movement of the handle when the rotational alignment difference meets an enablement criterion by transmitting to the slave system a control signal identifying the end effector position and orientation signals based on a current position and orientation of the handle, and disabling movement of the end effector in response to any movement of the handle comprises transmitting to the slave system a control signal identifying the end effector position and orientation signals determined from a previous position and orientation of the handle.

The at least one processor circuit may be further configured to receive an enablement signal.

The at least one processor circuit may be further configured to generate the enablement signal such that the enablement signal selectively has an active state or an inactive state.

The at least one processor circuit may be further configured to detect a change of the enablement signal from the inactive state to the active state and when the change is detected: store the current handle position signals ($\bar{P}_{MCURR}$) and the current handle orientation signals ($R_{MCURR}$) as master base position signals ($\bar{P}_{MBASE}$) and master base rotation signals ($R_{MBASE}$) respectively, in response to the change of the enablement signal, and store the new end effector position signals ($\bar{P}_{EENEW}$) and the new end effector orientation signals ($R_{EENEW}$) as end effector base position signals ($\bar{P}_{EEBASE}$) and end effector base rotation signals ($R_{EEBASE}$) respectively, in response to the change of the enablement signal.

The at least one processor circuit may be configured to compute the new end effector position signals ($\bar{P}_{EENEW}$) and the new end effector orientation signals ($R_{EENEW}$) by computing the new end effector position signals and the new end effector orientation signals according to the following relations:

$$\bar{P}_{EENEW} = A(\bar{P}_{MCURR} - \bar{P}_{MBASE}) + \bar{P}_{EEBASE}; \text{ and}$$

$$R_{EENEW} = R_{EEBASE} R_{MBASE}^{-1} R_{MCURR}.$$

At least one processor circuit may be further configured to cause the control signal to be further dependent on the state of the enablement signal, such that the control signal identifies the end effector position and orientation signals based on a current position and orientation of the handle when the alignment difference is less than the disablement criterion and the enablement signal is in the active state, and the control signal identifies the end effector position and orientation based on a previous position and orientation of the handle when the enablement signal is in the inactive state.

The at least one processor circuit may be further configured to produce annunciation signals for causing an annunciator to annunciate an indication of a relative rotational alignment of the handle and the end effector.

The at least one processor circuit may be configured to produce the annunciation signals by producing display control signals for causing a display to depict the relative alignment.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 9 is a flowchart of an alternative block of code optionally replacing the block of code shown at 204 and 206 in FIG. 8B;

DETAILED DESCRIPTION

Figure 1:
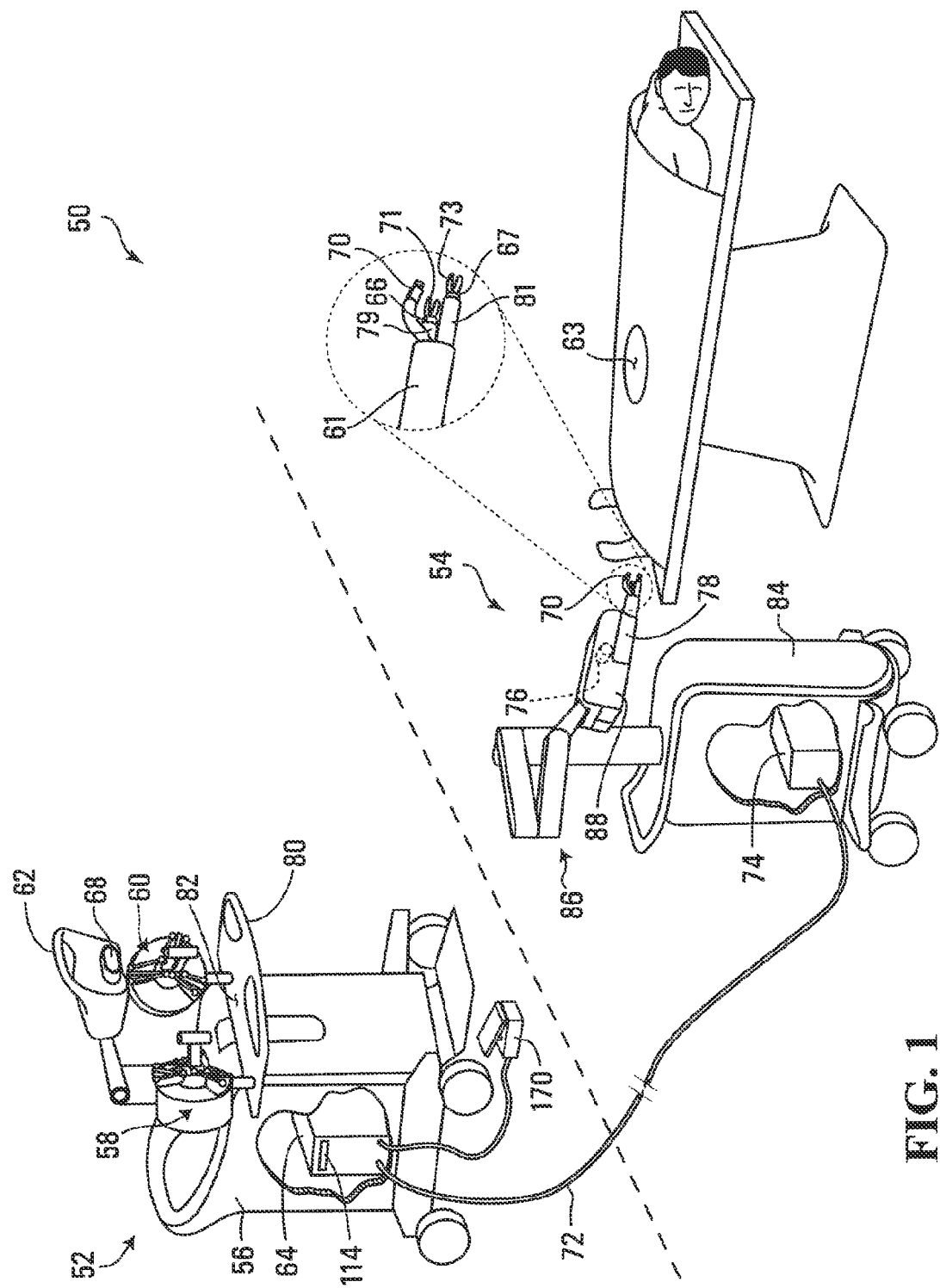
FIG. 1 is a pictorial representation of a laparoscopic surgery system according to one embodiment of the invention.

Referring to FIG. 1, a robotic control system in the form of a laparoscopic surgery system is shown generally at 50. The system includes a master subsystem 52 and a slave subsystem 54. The master subsystem 52 may be located anywhere in the world, but for the purposes of this description it will be considered to be in an operating room. The slave subsystem 54 is located in the operating room.

In the embodiment shown, the master subsystem 52 comprises a workstation 56 having first and second input devices 58 and 60 and a viewer 62 in communication with a master apparatus 64 comprising at least one processor. The first and second input devices 58 and 60 are operable to be actuated by respective hands of a user such as a surgeon, for example, who will perform the laparoscopic surgery by manipulating the first and second input devices of the master subsystem 52 to control corresponding laparoscopic tools 66 and 67 on the slave subsystem 54.

The viewer 62 may include an LCD display 68, for example, for displaying images acquired by a camera 70 on the slave subsystem 54, to enable the user to see the laparoscopic tools 66 and 67 inside the patient while manipulating the first and second input devices 58 and 60 to cause the tools to move in desired ways to perform the surgery. The first and second input devices 58 and 60 produce position and rotation signals that are received by the master apparatus 64 and the master apparatus produces slave control signals that are transmitted by wires 72 or wirelessly, for example, from the master subsystem 52 to the slave subsystem 54.

The slave subsystem 54 includes a slave computer 74 that receives the slave control signals from the master subsystem 52 and produces motor control signals that control motors 76 on a drive mechanism of a tool controller 78 of the slave subsystem, to extend and retract wires (not shown) of respective tool positioning devices 79 and 81 to position and to rotate the tools 66 and 67. Exemplary tool positioning devices and tools for this purpose are described in PCT/CA2013/001076, which is incorporated herein by reference. The tool positing devices 79 and 81 extend through an insertion tube 61, a portion of which is inserted through a small opening 63 in the patient to position end effectors 71 and 73 of the tools 66 and 67 inside the patient, to facilitate the surgery.

In the embodiment shown, the workstation 56 has a support 80 having a first flat surface 82 for supporting the first and second input devices 58 and 60 in positions that are comfortable to the user whose hands are actuating the first and second input devices 58 and 60.

In the embodiment shown, the slave subsystem 54 includes a cart 84 in which the slave computer 74 is located. The cart 84 has an articulated arm 86 mechanically connected thereto, with a tool holder mount 88 disposed at a distal end of the articulated arm.

In the embodiment shown, the first and second input devices 58 and 60 are the same, but individually adapted for left and right hand use respectively. In this embodiment, each input device 58 and 60 is an Omega.7 haptic device available from Force Dimension, of Switzerland. For simplicity, only input device 60 will be described, it is being understood that input device 58 operates in the same way.

Figure 2:
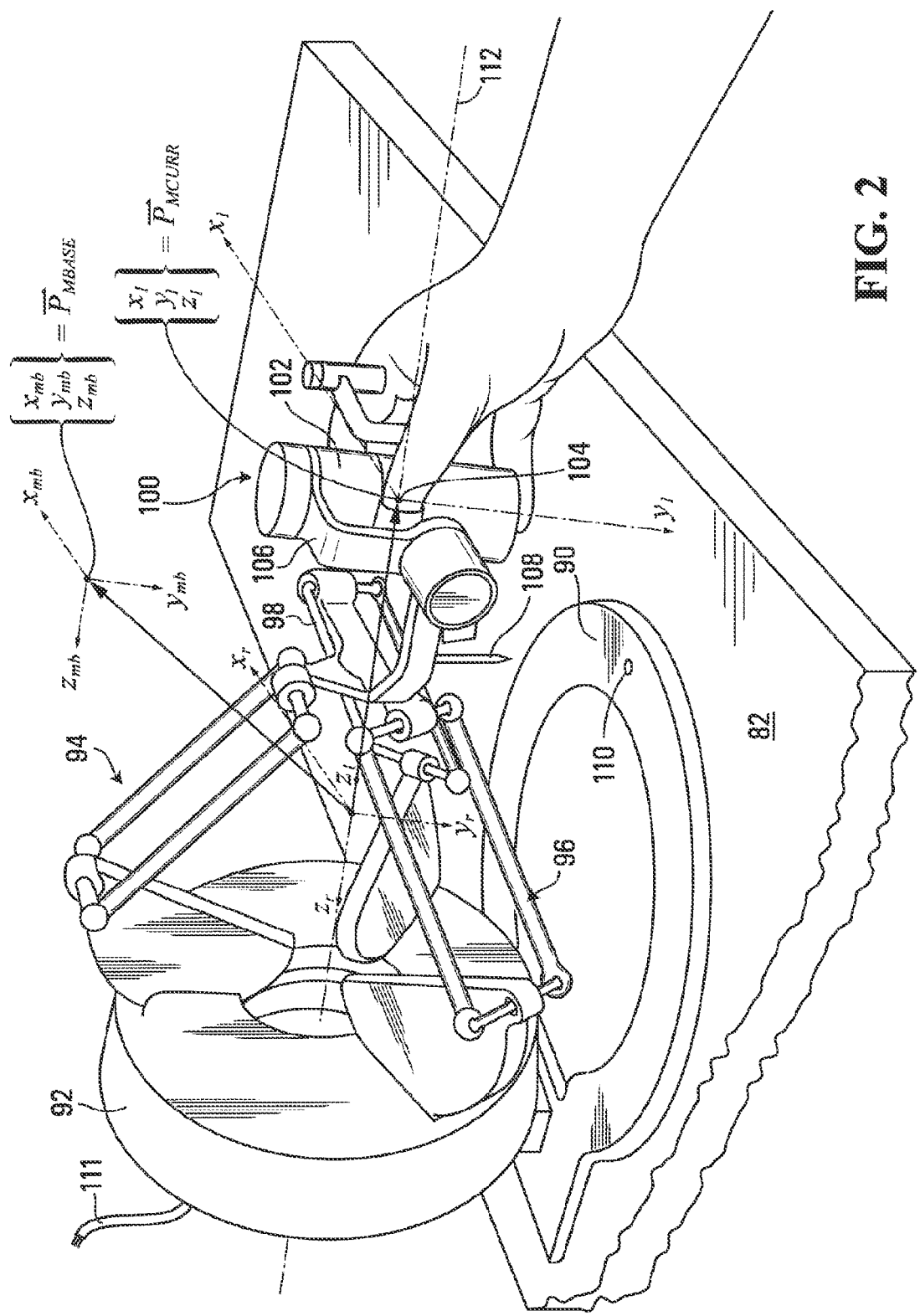
FIG. 2 is an oblique view of an input device of a master subsystem of the laparoscopic surgery system shown in FIG. 1.

Referring to FIG. 2, generally each Omega.7 haptic device includes a base plate 90 that supports a control unit 92 having arms 94, 96, 98 connected to a gimbal-mounted handle 102 that can be grasped by the hand of a user and rotated about orthogonal axes $x_1$, $y_1$ and $z_1$ of a first Cartesian reference frame having an origin at a point midway along the axis of a cylinder that forms part of the handle 102. This first Cartesian reference frame may be referred to as the handle reference frame. The origin may be referred to as the handle position 104.

The arms 94, 96, 98 facilitate translational movement of the handle 102 and hence the handle position 104, in space, and confine the movement of the handle position within a volume in space. This volume may be referred to as the handle translational workspace.

The handle 102 is mounted on a gimbal mount 106 having a pin 108. The base plate 90 has a calibration opening 110 for receiving the pin 108. When the pin 108 is received in the opening 110, the haptic device is in a calibration position that is defined relative to a fixed master Cartesian reference frame comprising orthogonal axes $x_r$, $y_r$, $z_r$ generally in the center of the handle translational workspace. In the embodiment shown, this master reference frame has an $x_r$-$z_r$ plane parallel to the flat surface 82 and a $y_r$ axis perpendicular to the flat surface. In the embodiment shown, the $z_r$ axis is parallel to the flat surface 82 and is coincident with an axis 112 passing centrally through the control unit 92 so that pushing and pulling the handle 102 toward and away from the center of the control unit 92 along the axis 112 in a direction parallel to the flat surface 82 is movement in the $z_r$ direction.

The control unit 92 has sensors (not shown) that sense the positions of the arms 94, 96, 98 and the rotation of the handle 102 about each of the $x_1$, $y_1$ and $z_1$ axes and produces signals representing the handle position 104 (i.e. the center of the handle 102) in the workspace and the rotational orientation of the handle 102 relative to the fixed master reference frame $x_r$, $y_r$, $z_r$. In this embodiment, these position and orientation signals are transmitted on wires 111 of a USB bus to the master apparatus 64. More particularly, the control unit 92 produces current handle position signals and current handle orientation signals that represent the current position and orientation of the handle 102 by a current handle position vector $\bar{P}_{MCURR}$ and a current handle rotation matrix $R_{MCURR}$, relative to the fixed master reference frame $x_r$, $y_r$, $z_r$.

For example, the current handle position vector $\bar{P}_{MCURR}$ is a vector $$\begin{Bmatrix} x_1 \\ y_1 \\ z_1 \end{Bmatrix},$$

where $x_1$, $y_1$, and $z_1$ represent coordinates of the controller position within the handle workspace relative to the fixed master reference frame, $x_r$, $y_r$, $z_r$.

The current handle rotation matrix $R_{MCURR}$ is a 3×3 matrix $$\begin{bmatrix} x_{1x} & y_{1x} & z_{1x} \\ x_{1y} & y_{1y} & z_{1y} \\ x_{1z} & y_{1z} & z_{1z} \end{bmatrix},$$

where the columns of the matrix represent the axes of the handle reference frame $x_1$, $y_1$, $z_1$ written in the fixed master reference frame $x_r$, $y_r$, $z_r$. $R_{MCURR}$ thus defines the current rotational orientation of the handle 102 in the handle translational workspace, relative to the $x_r$, $y_r$, $z_r$ master reference frame.

The current handle position vector $\bar{P}_{MCURR}$ and current handle rotation matrix $R_{MCURR}$ are transmitted in the current handle position and orientation signals on wires 111 of the USB bus, for example to the master apparatus 64 in FIG. 1.

In addition, in the embodiment shown, the master apparatus 64 is coupled to a footswitch 170 actuable by the user (surgeon) to provide a binary enablement signal to the master apparatus 64. When the footswitch 170 is not activated, i.e. not depressed, the enablement signal is in an active state and when the footswitch 170 is depressed the enablement signal is in an inactive state. The footswitch 170 thus controls the state of the enablement signal. As will be seen below, the enablement signal allows the user to cause the master apparatus 64 to selectively enable and disable movement of the end effectors in response to movement of the handles 102.

Figure 7:
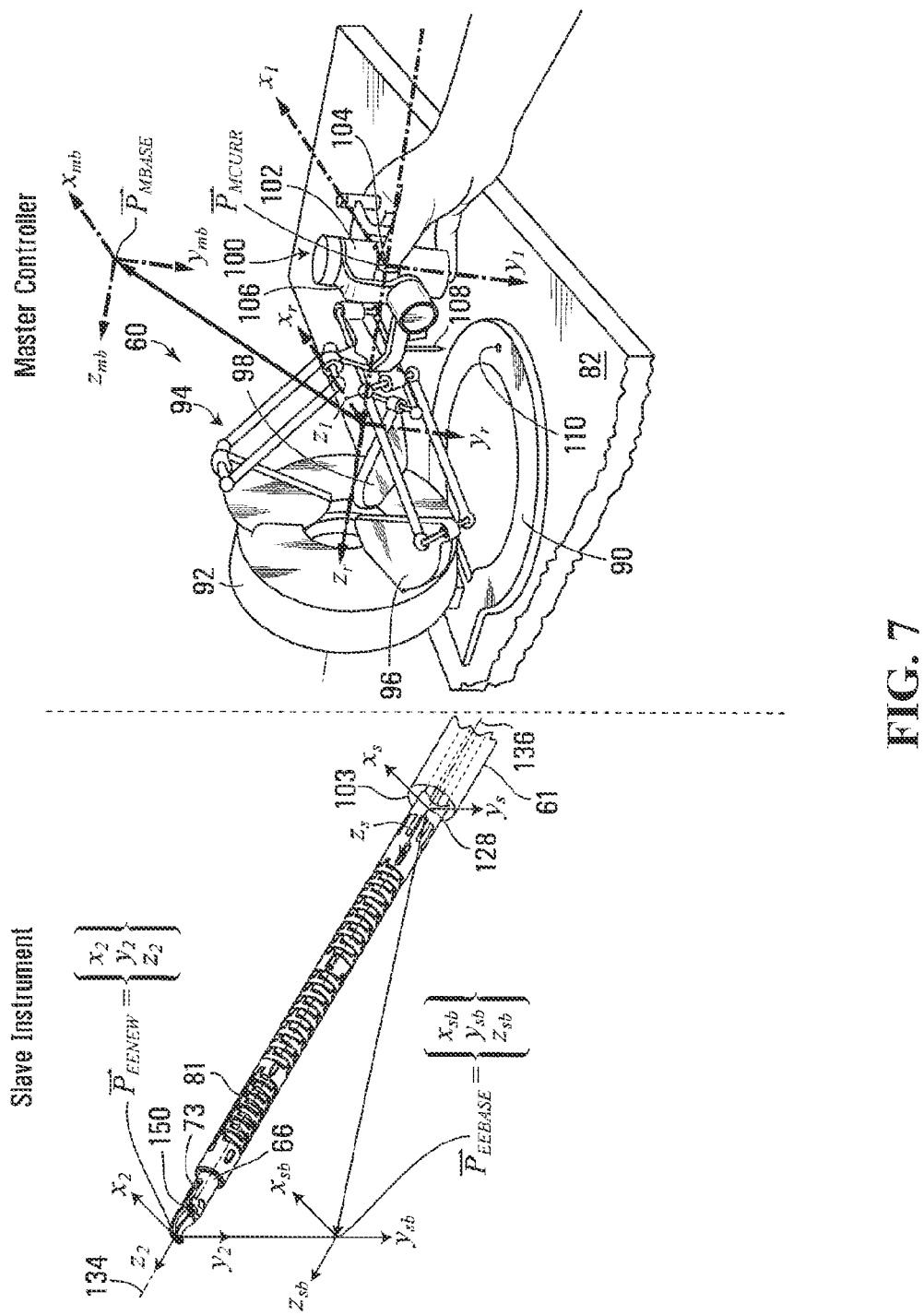
FIG. 7 is an oblique view of the input device shown in FIG. 2 and the tool holder shown in FIG. 4 showing relationships between base axes of the input device and the end effector.

Referring now to FIG. 7, the end effector 73 and related structures are described. The fixed slave reference frame has axes $x_s$, $y_s$ and $z_s$ which intersect at a point referred to as the slave fixed base position 128, lying on the longitudinal axis 136 of the insertion tube 61 and contained in a plane perpendicular to the longitudinal axis 136 and containing a distal edge 103 of the insertion tube 61. The $z_s$ axis is coincident with the longitudinal axis 136 of the insertion tube 61. The $x_s$-$z_s$ plane thus contains the longitudinal axis 136 of the insertion tube 61 and the $x_s$ and $y_s$ axes define a plane perpendicular to the longitudinal axis 136 of the insertion tube 61.

In the embodiment shown, end effector 73 includes a pair of gripper jaws. Orthogonal axes $x_2$, $y_2$ and $z_2$ of an end effector Cartesian reference frame have an origin at the intersection at a mid-point between gripper jaws of the end effector 73. The origin of the end effector reference frame may be referred to as the slave end effector position 150 relative to the fixed slave reference frame $x_s$, $y_s$, $z_s$.

Figure 3:
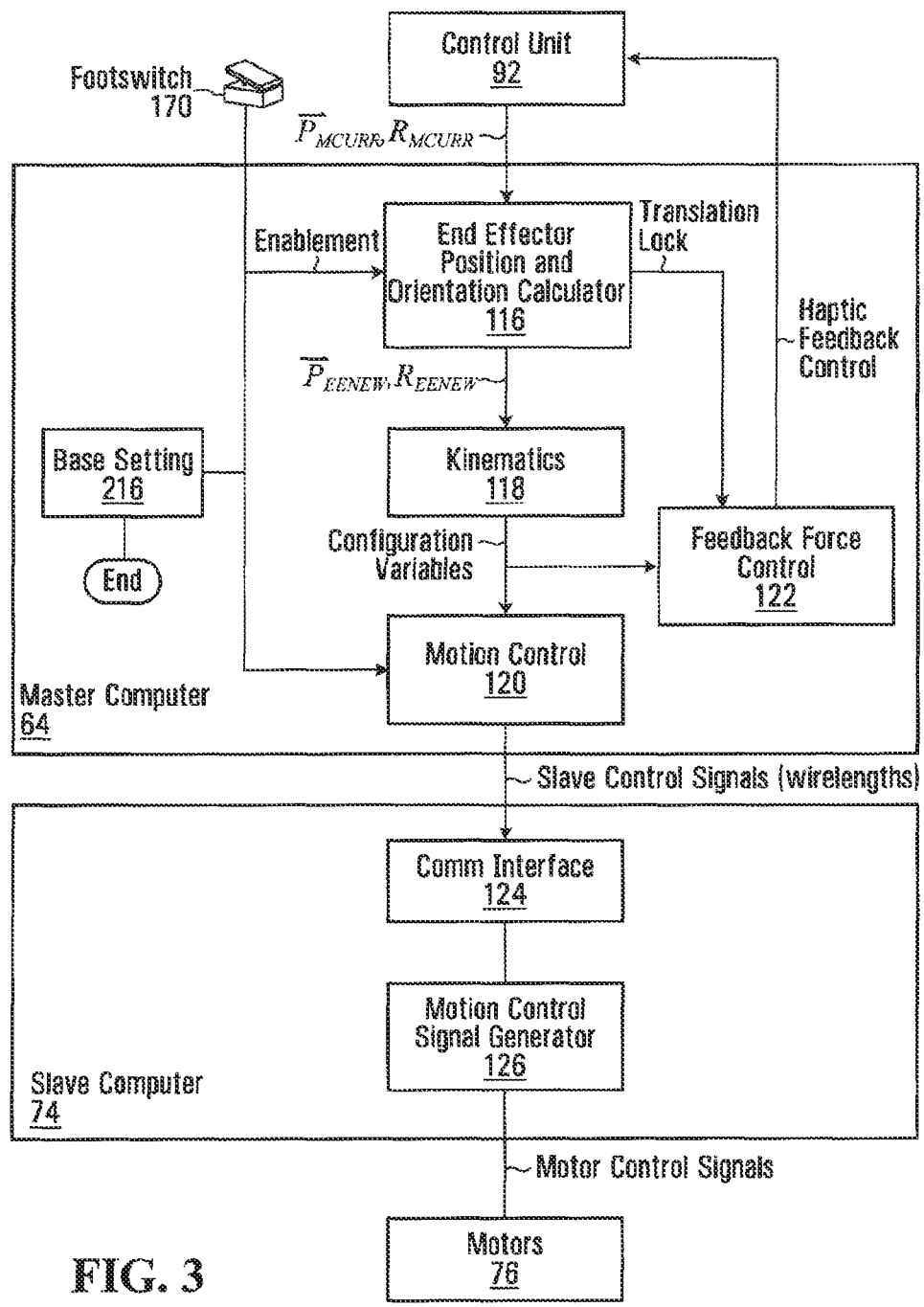
FIG. 3 is a block diagram illustrating certain functionality and certain signals produced and used by the system shown in FIG. 1.

New end effector positions and end effector orientations are calculated by the end effector position and orientation calculation block 116 shown in FIG. 3, in response to the current handle position signals $\bar{P}_{MCURR}$ and current handle orientation signals $R_{MCURR}$ and are represented by a new end effector position vector $\bar{P}_{EENEW}$ and an rotation matrix $R_{EENEW}$, relative to the $x_s$, $y_s$, $z_s$ fixed slave reference frame.

For example, the new end effector position vector $\bar{P}_{EENEW}$ is a vector $$\begin{Bmatrix} x_2 \\ y_2 \\ z_2 \end{Bmatrix},$$

where $x_2$, $y_2$, and $z_2$ represent coordinates of the end effector position within the end effector workspace relative to the $x_s$, $y_s$, $z_s$ fixed slave reference frame.

The end effector rotation matrix $R_{EENEW}$ is a 3×3 matrix $$\begin{bmatrix} x_{2x} & y_{2x} & z_{2x} \\ x_{2y} & y_{2y} & z_{2y} \\ x_{2z} & y_{2z} & z_{2z} \end{bmatrix},$$

where the columns of the $R_{EENEW}$ matrix represent the axes of the end effector reference frame $x_2$, $y_2$, $z_2$ written in the fixed slave reference frame $x_s$, $y_s$, $z_s$. $R_{EENEW}$ thus defines a new orientation of the end effector 73 in the workspace, relative to the $x_s$, $y_s$, $z_s$ reference frame.

Referring back to FIG. 1, in the embodiment shown, the master apparatus 64 is controlled by program codes stored on a non-transitory computer readable medium such as a disk drive 114. The codes direct the master apparatus 64 to perform various functions. Referring to FIGS. 1 and 3, these functions may be grouped into categories and expressed as functional blocks of code including an end effector position and orientation calculation block 116, a kinematics block 118, a motion control block 120, a feedback force control block 122, and a base setting block 216, all stored on the disk drive 114 of the master apparatus 64. For ease of description, these blocks are shown as functional blocks within the master apparatus 64 in FIG. 3. These functional blocks are executed separately but in the same manner for each input device 58 and 60. The execution of these functional blocks for only input device 60 and end effector 73 will be described, it being understood they are separately executed in the same way for input device 58 and end effector 71 to achieve control of end effectors 73 and 71 by right and left hands respectively of the user.

Generally, the end effector position and orientation calculation block 116 includes codes that direct the master apparatus 64 to produce new end effector position and rotation signals, later referred to herein as $\bar{P}_{EENEW}$ and $R_{EENEW}$, and includes codes that direct the master apparatus 64 to produce a translation lock signal for receipt by the feedback force control block 122.

The kinematics block 118 includes codes that direct the master apparatus 64 to produce configuration variables in response to the newly calculated end effector position and rotation signals.

The motion control block 120 includes codes that direct the master apparatus 64 to produce the slave control signals, in response to the configuration variables.

The feedback force control block 122 directs the master apparatus 64 to receive the translation lock signal from the end effector position and orientation calculation block 116 and to receive the configuration variables from the kinematics block 118 and to produce a haptic feedback control signal that is provided to the control unit 92 to cause the control unit to present a force to the user if the user tries to cause translational movement of the handle 102. This impedes translational movement of the handle 102 but allows the handle 102 to be rotated to allow it to be brought into rotational alignment with the end effector 73.

The base setting block 216 is executed asynchronously, whenever the enablement signal transitions from an inactive state to an active state, such as when the user releases the footswitch 170. The base setting block 216 directs the master apparatus 64 to set new reference positions and orientations for the handle 102 and end effector 73, respectively as will be described below.

Referring back to FIG. 1, in the embodiment shown, the slave control signals represent wire length values indicating how much certain wires of a given tool positioning device 81 of the slave subsystem 54 must be extended or retracted to cause the end effector 73 of the tool 67 to be positioned and rotated in a manner determined by positioning and rotating the corresponding input device 60.

Referring to FIGS. 1 and 3, the slave control signals representing the wire length values are transmitted to the slave computer 74, which has its own computer readable medium encoded with communication interface codes 124 for directing the slave computer to receive the slave control signals from the master apparatus 64. The computer readable medium is also encoded with motor control signal generator codes 126 for causing the slave computer 74 to generate motor control signals for controlling the motors 76 on the tool controller 78 to extend and retract the wires controlling the attached tool positioning device 81 according to the wire length values represented by the control signals from the master apparatus 64.

The kinematics block 118 receives newly calculated end effector position and orientation signals ($\vec{P}_{EENEW}$ and $R_{EENEW}$) each time the end effector position and orientation calculation block 116 is executed. In response, the kinematics block 118 produces the configuration variables described below.

Referring to FIG. 3, generally, the codes in the kinematics block 118 direct the master apparatus 64 to calculate values for the above configuration variables in response to the end effector position and rotation signals $\vec{P}_{EENEW}$ and $R_{EENEW}$ produced by the end effector position and orientation calculation block 116 and these calculated configuration values generally define a tool holder pose required to position end effector 73 at a desired location and at a desired orientation in its workspace.

Figure 4:
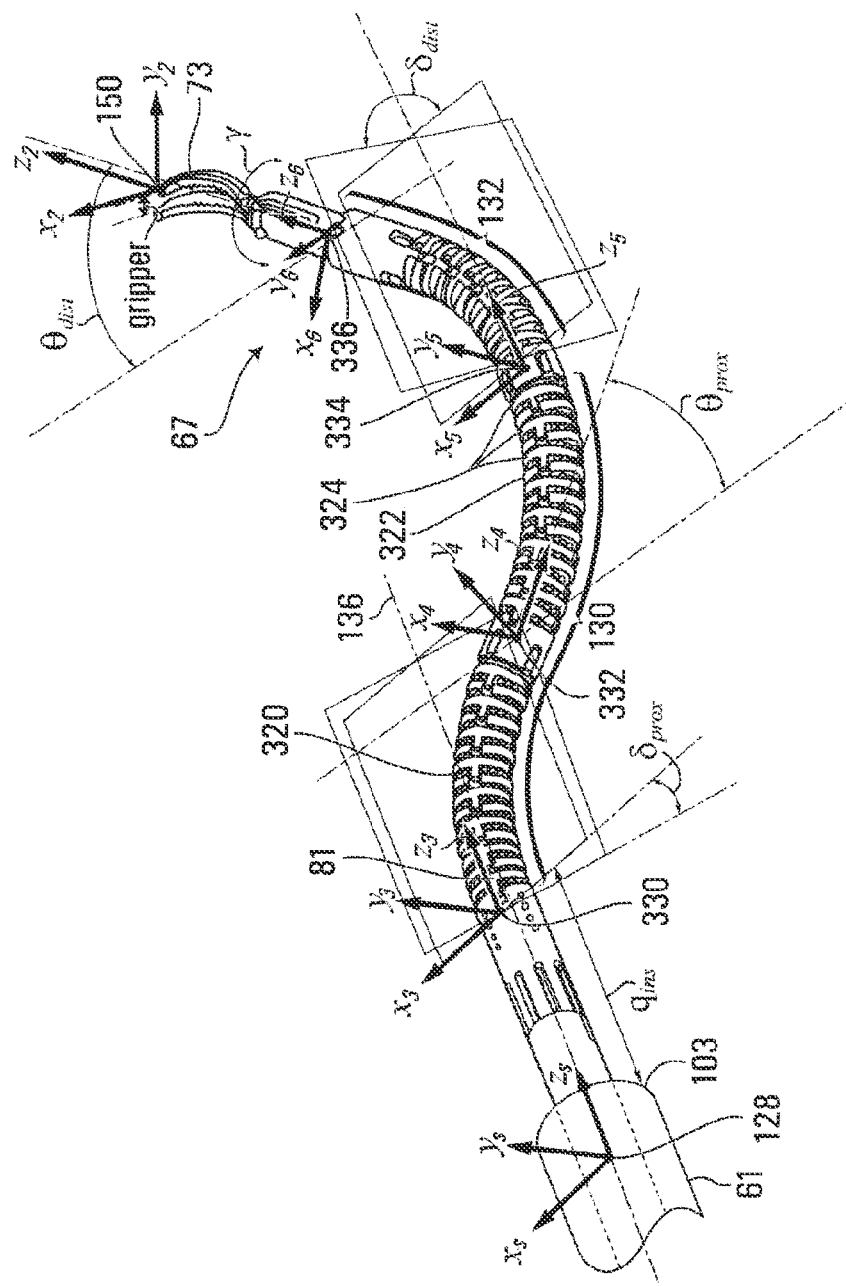
FIG. 4 is an oblique view of a tool holder with a tool in the form of an end effector held thereby, in an insertion tube of the laparoscopic surgery system shown in FIG. 1.

Referring to FIG. 4, the tool positioning device 81 has a first articulated segment 130, referred to as an s-segment and a second articulated segment 132 referred to as a distal segment. The segments 130 and 132 each include a plurality of "vertebra" 324.

The s-segment 130 begins at a distance from the insertion tube 61, referred to as the insertion distance $q_{ins}$, which is the distance between the fixed slave base position 128 defined as the origin of the slave fixed base reference frame $x_s$, $y_s$, $z_s$ and a first position 330 at the origin of a first position reference frame $x_3$, $y_3$, and $z_3$. The insertion distance $q_{ins}$ represents an unbendable portion of the tool positioning device 81 that extends out of the end of the insertion tube 61. In the embodiment shown, the insertion distance $q_{ins}$ may be about 10-20 mm, for example. In other embodiments, the insertion distance $q_{ins}$ may be longer or shorter, varying from 0-100 mm, for example.

The s-segment 130 extends from the first position 330 to a third position 334 defined as an origin of a third reference frame having axes $x_5$, $y_5$, and $z_5$ and is capable of assuming a smooth S-shape when control wires (not shown) inside the s-segment 130 are pushed and pulled. The s-segment 130 has a mid-point at a second position 332, defined as the origin of a second position reference frame having axes $x_4$, $y_4$, $z_4$. The s-segment 130 has a length $L_1$, which in the embodiment shown may be about 65 mm, for example.

The distal segment 132 extends from the third position 334 to a fourth position 336 defined as an origin of a fourth reference frame having axes $x_6$, $y_6$, $z_6$. The distal segment 132 has a length $L_2$, which in the embodiment shown may be about 23 mm, for example.

The tool 67 also has an end effector length, which in the embodiment shown is a gripper length $L_3$ that extends from the fourth position 336 to the end effector position 150 defined as the origin of axes $x_2$, $y_2$, and $z_2$. The gripper length $L_3$, in this embodiment, may be about 25 mm, for example. The slave base position 128, first position 330, second position 332, third position 334, fourth position 336 and end effector position 150 may collectively be referred to as tool reference positions.

As explained in PCT/CA2013/001076, hereby incorporated herein by reference in its entirety, by pushing and pulling on certain control wires inside the tool positioning devices 79 and 81, the s-segment 130 can be bent into any of various degrees of an S-shape, from straight as shown in FIG. 7 to a partial S-shape as shown in FIG. 4 to a full S-shape. The s-segment 130 is sectional in that it has a first section 320 and a second section 322 on opposite sides of the second position 332. The first and second sections 320 and 322 lie in a first bend plane containing the first position 330, second position 332, and third position 334. The first bend plane is at an angle $\delta_{prox}$ to the $x_s$-$z_s$ plane of the fixed slave reference frame. The first section 320 and second section 322 are bent in the first bend plane through opposite but equal angles $\theta_{prox}$ such that no matter the angle $\theta_{prox}$ or the bend plane angle $\delta_{prox}$, the $z_5$ axis of the third position 334 is always parallel to and aligned in the same direction as the $z_s$ axis of the fixed slave base position 128. Thus, by pushing and pulling on the control wires within the tool positioning device 81, the third position 334 can be placed at any of a number of discrete positions within a cylindrical volume in space. This volume may be referred to as the s-segment workspace.

In addition, the distal segment 132 lies in a second bend plane containing the third position 334 and the fourth position 336. The second bend plane is at an angle $\delta_{dist}$ to the $x_s$-$z_s$ plane of the fixed slave reference frame. The distal segment 132 is bent in the second bend plane at an angle $\theta_{dist}$. Thus, by pushing and pulling the control wires within the tool positioning device 81, the fourth position 336 can be placed within another volume in space. This volume may be referred to as the distal workspace. The combination of the s-segment workspace plus the distal workspace can be referred to as the tool positioning device workspace, as this represents the total possible movement of the tools 66 and 67 as effected by the respective tool positioning devices 79 and 81.

The distance between the fourth position 336 and the end effector position 150 is the distance between the movable portion of the distal segment 132 and the tip of the gripper end effector 73 in the embodiment shown, i.e. the length $L_3$. Generally, the portion of the gripper between the fourth position 336 and the end effector position 150 ($L_3$) will be unbendable.

In the embodiment shown, the end effector 73 is a gripper jaw tool that is rotatable about the $z_2$ axis in the $x_2$-$y_2$ plane of the end effector reference frame, the angle of rotation being represented by an angle $\gamma$ relative to the positive $x_2$ axis. Finally, the gripper jaws may be at any of varying degrees of openness from fully closed to fully open (as limited by the hinge). The varying degrees of openness may be defined as the "gripper".

In summary therefore, the configuration variables provided by the kinematic block 118 codes are as follows:

$q_{ins}$: represents a distance from the slave base position 128 defined by axes $x_s$, $y_s$, and $z_s$ to the first position 330 defined by axes $x_3$, $y_3$ and $z_3$ where the s-segment 130 of the tool positioning device 81 begins;

$\delta_{prox}$: represents a first bend plane in which the s-segment 130 is bent relative to the $x_s$-$y_s$ plane of the fixed slave reference frame;

$\theta_{prox}$: represents an angle at which the first and second sections 320 and 322 of the s-segment 130 is bent in the first bend plane;

$\delta_{dist}$: represents a second bend plane in which the distal segment 132 is bent relative to the $x_s$-$y_s$ plane of the fixed slave reference frame;

$\theta_{dist}$: represents an angle through which the distal segment 132 is bent in the second bend;

$\gamma$: represents a rotation of the end effector 73 about axis $z_2$; and

Gripper: represents a degree of openness of the gripper jaws of the end effector 73. (This is a value which is calculated in direct proportion to a signal produced by an actuator (not shown) on the handle 102 indicative of an amount of pressure the operator exerts by squeezing the handle).

To calculate the configuration variables, it will first be recalled that the end effector rotation matrix $R_{EENEW}$ is a 3×3 matrix:

$$\begin{bmatrix} x_{2x} & y_{2x} & z_{2x} \\ x_{2y} & y_{2y} & z_{2y} \\ x_{2z} & y_{2z} & z_{2z} \end{bmatrix}.$$

Since the last column of $R_{EENEW}$ is the z-axis of the end effector reference frame written relative to the fixed slave reference frame $x_s$, $y_s$ and $z_s$, the values $\theta_{dist}$, $\delta_{dist}$, and $\gamma$ associated with the distal segment 132 can be calculated according to the relations:

$$\theta_{dist} = \frac{\pi}{2} - a\tan2\left(\sqrt{z_{2x}^2 + z_{2y}^2}, z_{2z}\right) \quad (2)$$

$$\delta_{dist} = -a\tan2(z_{2y}, z_{2x}) \quad (3)$$

If $|\delta_{dist}| > \frac{\pi}{2}$ $$\gamma = a\tan2(-y_{2z}, x_{2z}) - \delta_{dist} + \pi \quad (4a)$$

else $$\gamma = a\tan2(y_{2z}, -x_{2z}) - \delta_{dist} \quad (4b)$$

These values can then be used to compute the locations of the third position 334, the fourth position 336, and the end effector position 150 relative to the fixed slave base position 128. The locations may be expressed in terms of vectors $\bar{p}_{3/s}$ from the fixed slave base position 128 to the first position 330, $\bar{p}_{4/3}$ from the third position 334 to the fourth position 336, and $\bar{p}_{5/4}$ from the fourth position 336 to the end effector position 150. $\bar{p}_{3/s}$ is then calculated from $\vec{P}_{EENEW}$ as follows:

$$\bar{p}_{3/s} = \bar{p}_{EENEW} - \bar{p}_{4/3} - \bar{p}_{5/4}, \quad (5)$$

$$\bar{p}_{4/3} \cdot \bar{i} = \frac{-L_2 \cos\delta_{dist}(\sin\theta_{dist} - 1)}{\frac{\pi}{2} - \theta_{dist}} \quad (6a)$$

$$\bar{p}_{4/3} \cdot \bar{j} = \frac{L_2 \sin\delta_{dist}(\sin\theta_{dist} - 1)}{\frac{\pi}{2} - \theta_{dist}} \quad (6b)$$

$$\bar{p}_{4/3} \cdot \bar{k} = \frac{L_2 \cos\delta_{dist}(\theta_{dist})}{\frac{\pi}{2} - \theta_{dist}} \quad (6c)$$

$$\bar{p}_{5/4} \cdot \bar{i} = L_3 \cos(\delta_{dist})\cos(\theta_{dist}) \quad (7a)$$

$$\bar{p}_{5/4} \cdot \bar{j} = -L_3 \sin(\delta_{dist})\cos(\theta_{dist}) \quad (7b)$$

$$\bar{p}_{5/4} \cdot \bar{k} = L_3 \sin(\theta_{dist}), \quad (7c)$$

where:
$\bar{i}$ is a unit vector in the x direction;
$\bar{j}$ is a unit vector in the y direction; and
$\bar{k}$ is a unit vector in the z direction.

Once the vector from the fixed slave base position 128 to the third position 334 ($\bar{p}_{3/s}$) is known, the configuration variables, $\delta_{prox}$ and $\theta_{prox}$, for the s-segment 130 can be found. The configuration variable $\delta_{prox}$ associated with the s-segment 130 is calculated by solving the following two equations for $\delta_{prox}$:

$$\bar{p}_{3/s} \cdot \bar{i} = \frac{-L_1 \cos\delta_{prox}(\sin\theta_{prox} - 1)}{\frac{\pi}{2} - \theta_{prox}} \quad (8a)$$

$$\bar{p}_{3/s} \cdot \bar{j} = \frac{L_1 \sin\delta_{prox}(\sin\theta_{prox} - 1)}{\frac{\pi}{2} - \theta_{prox}}. \quad (8b)$$

The ratio of (8b) and (8a) gives $$\delta_{prox} = a\tan2(-\bar{p}_{3/s} \cdot \bar{j}, \bar{p}_{3/s} \cdot \bar{i}), \quad (9)$$

where $\bar{i}$ and $\bar{j}$ are unit vectors in the x and y directions respectively.

A closed form solution cannot be found for $\theta_{prox}$, thus $\theta_{prox}$ must be found with a numerical equation solution to either of equations (8a) or (8b). A Newton-Raphson method, being a method for iteratively approximating successively better roots of a real-valued function, may be employed, for example. The Newton-Raphson method can be implemented using the following equations:

$$f(\theta_{prox}) = \frac{L_1}{\frac{\pi}{2} - \theta_{prox}} \cos\delta_{prox}(1 - \sin\theta_{prox}) - \bar{p}_{3/s} \cdot \bar{i} = 0, \quad (10)$$

where $\bar{i}$ is the unit vector in the x direction.

The equation (10) is equation (8a) rewritten in the form $f(\theta_{prox})=0$. The Newton-Raphson method tends to converge very quickly because in the range $0<\theta_{prox}<\pi$, the function has a large radius of curvature and has no local stationary points. Following the Newton-Raphson method, successive improved estimates of $\theta_{prox}$ can be made iteratively to satisfy equation (10) using the following relationship:

$$\theta_{n+1} = \theta_n - \frac{f(\theta_n)}{f'(\theta_n)} \quad (11)$$

Finally, upon determination of $\theta_{prox}$, the following equation can be used to find $q_{ins}$, $$q_{ins} = -\bar{p}_{3/s} \cdot \bar{k} - \frac{L_1 \cos\theta_{prox}}{\frac{\pi}{2} - \theta_{prox}}, \quad (12)$$

where:

$\bar{k}$ is the unit vector in the z direction;

$\bar{p}_{3/s} \cdot \bar{k}$ is the dot product of the vector $\bar{p}_{3/s}$ and the unit vector $\bar{k}$.

Figure 6:
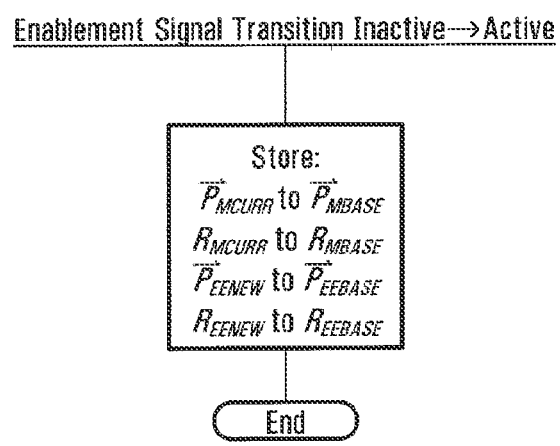
FIG. 6 is a block diagram of a storage routine executed by the master apparatus in response to detection of a signal transition of an enablement signal produced in response to user input.

The codes in the kinematics block 118 shown in FIG. 6 direct the master apparatus 64 to calculate values for the above configuration variables in response to the end effector position and orientation signals $\bar{P}_{EENEW}$ and $R_{EENEW}$ produced by the end effector position and orientation calculation block 116 and these calculated configuration variables generally define a tool positioning device pose required to position the end effector 73 at a desired location and at a desired orientation in the end effector workspace.

It will be appreciated that configuration variables are produced for each end effector 71 and 73 and therefore in the embodiment shown, two sets of configuration variables which will be referred to as left and right configuration variables respectively are produced and forwarded or otherwise made available to the motion control block 120 and the feedback force control block 122.

Figure 5:
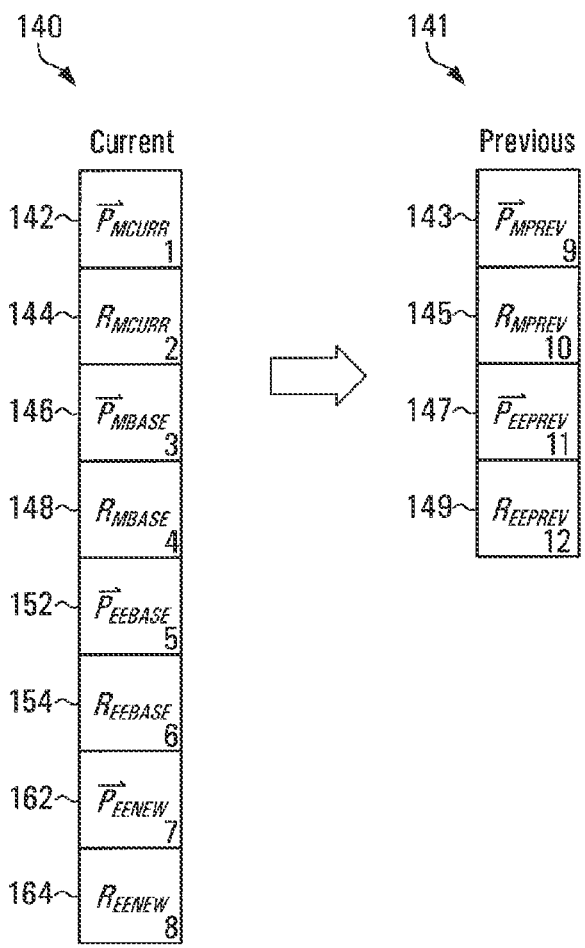
FIG. 5 is a schematic representation of current and previous value buffers maintained by a master apparatus of the system shown in FIG. 1 and updated according to the functions shown in FIGS. 6, 8A and 8B.

Referring to FIG. 5, the master apparatus 64 queries the control unit 92 for the handle position vector $\bar{P}_{MCURR}$ and handle rotation matrix $R_{MCURR}$ periodically, at a sample rate of about 1 kHz. These values are stored by the master apparatus 64 in a first "current" buffer 140 having a first store 142 storing the three values representing the currently acquired handle position vector $\bar{P}_{MCURR}$ and a second store 144 storing the nine values representing the acquired handle rotation matrix $R_{MCURR}$.

Referring to FIGS. 2 and 5, the master apparatus 64 also stores values $x_{mb}$, $y_{mb}$, $z_{mb}$ representing a definable master base position represented by a base position vector $\bar{P}_{MBASE}$ in a third store 146 and stores values representing a definable master base rotation matrix $R_{MBASE}$ in a fourth store 148. The master apparatus 64 initially causes the definable master base position vector $\bar{P}_{MBASE}$ to be set equal to the current handle position vector $\bar{P}_{MCURR}$ on startup of the system and causes the definable master base rotation matrix $R_{MBASE}$ to define an orientation that is the same as the current orientation defined by the handle rotation matrix $R_{MCURR}$ associated with the current handle rotation, on startup of the system.

Initially, therefore:

$$\bar{P}_{MBASE} = \bar{P}_{MCURR}; \text{ and}$$

$$R_{MBASE} = R_{MCURR}$$

Thereafter, the master base position $\bar{P}_{MBASE}$ and the master base rotation matrix $R_{MBASE}$ are maintained at the same values as on startup until the enablement signal is activated, such as by the footswitch (170 in FIGS. 1 and 3), which causes the enablement signal to transition from the inactive state to the active state. In response, the base setting block 216 in FIG. 6 is executed to change the master base position vector $\bar{P}_{MBASE}$ and master base rotation matrix $R_{MBASE}$ to the currently acquired master position $\bar{P}_{MCURR}$ and currently acquired master orientation $R_{MCURR}$ respectively.

Referring to FIGS. 5 and 7, the master apparatus 64 further stores values $x_{sb}$, $y_{sb}$, $z_{sb}$ representing a definable slave base position $\bar{P}_{EEBASE}$ in a fifth store 152 and stores values representing a definable slave base rotation $R_{EEBASE}$ in a sixth store 154. The master apparatus 64 initially causes the definable slave base position vector $\bar{P}_{EEBASE}$ to be set equal to the new end effector position vector $\bar{P}_{EENEW}$ and causes the definable slave base rotation matrix $R_{EEBASE}$ to define an orientation that is the same as the orientation defined by the new end effector rotation matrix $R_{EENEW}$, on startup of the system.

Initially, therefore:

$$\bar{P}_{EEBASE} = \bar{P}_{EENEW}; \text{ and}$$

$$R_{EEBASE} = R_{EENEW}$$

In other words, the slave base reference frame and the end effector reference frame coincide at startup.

The slave base position $\bar{P}_{EEBASE}$ and slave base rotation matrix $R_{EEBASE}$ are maintained at the same values as on startup until the enablement signal is activated such as by the footswitch (170 in FIGS. 1 and 3), which causes the enablement signal to transition from the inactive state to the active state. In response, the base setting block 216 in FIG. 6 changes the slave base position vector $\bar{P}_{EEBASE}$ and slave rotation matrix $R_{EEBASE}$ to the newly calculated end effector position vector $\bar{P}_{EENEW}$ and newly calculated end effector rotation matrix $R_{EENEW}$.

Figure 8A:
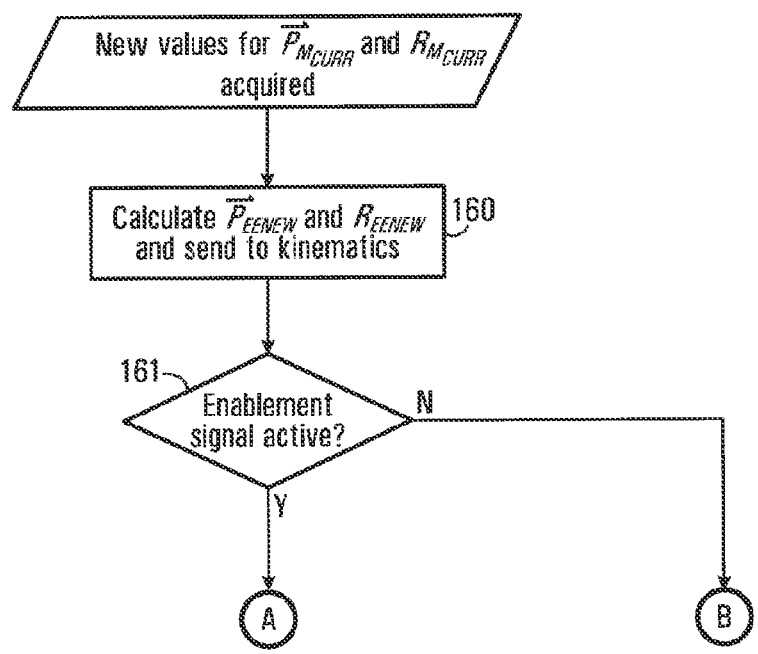
FIGS. 8A-8B are successive portions of a flowchart representing codes executed by a master apparatus of the system shown in FIG. 1, to provide for computation of an alignment difference between the input device shown in FIG. 2 and the end effector shown in FIG. 4 and for controlling translational movement of the end effector and for controlling the type of control signals sent to a slave subsystem of the laparoscopic surgery system shown in FIG. 1, based on the computed alignment difference.
Figure 8B:
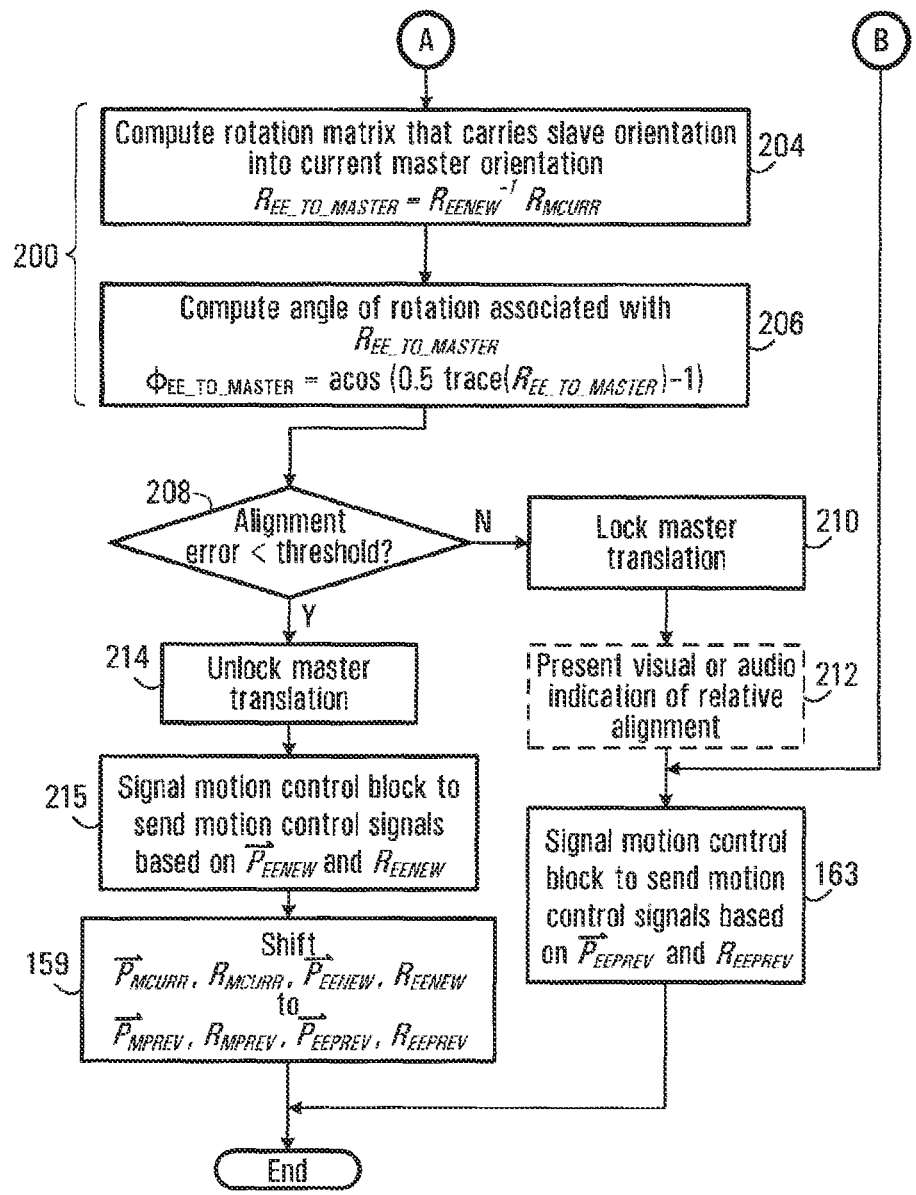

Referring to FIGS. 8A and 8B, the end effector position and orientation calculation block 116 is executed each time a set of new values for $\bar{P}_{MCURR}$ and $R_{MCURR}$ are acquired from the control unit 92. The end effector position and orientation calculation block 116 directs the master apparatus 64 to produce and store, in a seventh store 162 in FIG. 5, values representing the new end effector position vector $\bar{P}_{EENEW}$ and to produce and store, in an eighth store 164 in FIG. 5, values representing the desired end effector rotation matrix $R_{EENEW}$.

After new values for $\bar{P}_{MCURR}$ and $R_{MCURR}$ are acquired from the control unit 92, block 160 in FIG. 8A directs the master apparatus 64 to generate new end effector position signals $\bar{P}_{EENEW}$ and new end effector orientation signals $R_{EENEW}$ representing a desired end effector position 150 and desired end effector orientation, relative to the slave base position 128 and the slave base orientation.

The new end effector position signals $\bar{P}_{EENEW}$ and new end effector orientation signals $R_{EENEW}$ are calculated according to the following relations:

$$\bar{P}_{EENEW} = A(\bar{P}_{MCURR} - \bar{P}_{MBASE}) + \bar{P}_{EEBASE}$$

and $$R_{EENEW} = R_{EEBASE} R_{MBASE}^{-1} R_{MCURR}$$

Where: $\bar{P}_{EENEW}$ is the new end effector position vector that represents the new desired position of the end effector 73 in the end effector workspace, relative to the slave base reference frame;

A is a scalar value representing a scaling factor in translational motion between the master and the slave;

$\bar{P}_{MCURR}$ is the current representation of the handle position vector stored in the first store 142, the handle position vector being relative to the master reference frame;

$\bar{P}_{MBASE}$ is the last-saved position vector $\bar{P}_{MCURR}$ for the handle that was saved upon the last inactive to active state transition of the enablement signal such as by release of the footswitch 170 or on system initialization or by operation of a control interface by the user;

$\bar{P}_{EEBASE}$ is the last-saved position vector $\bar{P}_{EENEW}$ for the end effector 73 that was saved upon the last inactive to active state transition of the enablement signal;

$R_{EENEW}$ is the new end effector rotation matrix representing the current orientation of the end effector 73 relative to the slave reference frame;

$R_{EEBASE}$ is the rotation matrix representing the last-saved rotation of the end effector 73 saved upon the last inactive to active state transition of the enablement signal;

$R_{MBASE}^{-1}$ is the inverse of rotation matrix $R_{MBASE}$, where $R_{MBASE}$ is a rotation matrix representing the last-saved rotation of the handle 102 saved upon the last inactive to active state transition of the enablement signal;

$R_{MCURR}$ is the currently acquired rotation matrix representing the orientation of the handle 102 relative to the master reference frame;

When the enablement signal is in the active state, as determined at block 161 in FIG. 8A, the master apparatus 64 is directed to the blocks shown generally at 200 in FIG. 8B to detect a rotational alignment difference, i.e. a difference, between the orientation of the handle 102 ($R_{MCURR}$) and the newly calculated end effector orientation ($R_{EENEW}$), the difference representing a difference in physical alignment of these entities.

A difference in alignment can comprise any single degree of freedom or combination of degrees of freedom of any representation of orientation. In the general case, the alignment error would be computed considering all three orientation degrees of freedom. This case would, therefore, require that to be aligned, the reference frames described by $R_{EENEW}$ and $R_{MCURR}$ be coincident.

In the general case, blocks 204 and 206 shown in FIG. 8B could be carried out to obtain the alignment error.

Block 204 directs the master apparatus 64 to compute a rotation matrix that carries the newly calculated end effector orientation into the current handle orientation ($R_{EE\_TO\_MASTER}$) by the relation:

$$R_{EE\_TO\_MASTER} = R_{EENEW}^{-1} R_{MCURR}$$

Where: $R_{EENEW}^{-1}$ is the inverse matrix of the end effector rotation matrix $R_{EENEW}$ represented by a 3×3 matrix stored in the eighth store 164; and $R_{MCURR}$ is the current handle rotation matrix represented by the 3×3 matrix stored in the second store 144.

Then, block 206 directs the master apparatus 64 to compute an angle of rotation associated with $R_{EE\_TO\_MASTER}$ ($\varphi_{EE\_TO\_MASTER}$) by the relation:

$$\varphi_{EE\_TO\_MASTER} = a\cos(0.5\ \text{trace}(R_{EE\_TO\_MASTER}) - 1)$$

This angle of rotation ($\varphi_{EE\_TO\_MASTER}$) represents the alignment difference between the orientation of the handle 102 and the newly calculated end effector orientation.

In a special case, applicable to the embodiment described here, it is desirable that to be aligned, only the z-axes of the reference frames described by $R_{EENEW}$ and $R_{MCURR}$ be coincident. In this case the master handle and the slave end effector point in the same direction and the roll about their z-axis is not considered.

In this special case therefore, blocks 204 and 206 shown in FIG. 8B are replaced with block 205 shown in FIG. 9 which involves the following computation $$\varphi_{EE\_TO\_MASTER} = a\cos(R_{EENEW}(1,3) \ast R_{MCURR}(1,3) + R_{EENEW}(2,3) \ast R_{MCURR}(2,3) + R_{EENEW}(3,3) \ast R_{MCURR}(3,3))$$

This computation represents the angle obtained from the dot product of the z-axes of the master and slave reference frames.

After determining the angle of rotation $\varphi_{EE\_TO\_MASTER}$, using either the generic method shown in blocks 204 and 206 or the method that assumes the z axes of the master and slave reference frames are aligned, block 208 directs the master apparatus 64 to determine whether the alignment difference meets a criterion. A first criterion may be that the alignment difference is not less than a threshold value, and a second criterion may be that the alignment difference is less than the threshold value, for example.

If the alignment difference meets the second criterion (i.e. is less than the threshold value), block 214 directs the master apparatus 64 to release any previously produced translation lock signal locking the master input device 60 by setting the translation lock signal inactive, thereby signaling the feedback force control block 122 of FIG. 3 to stop providing haptic feedback control signals that may have been preventing translational movement of the handle 102.

Then block 215 directs the master apparatus 64 to signal the motion control block 120 of FIG. 3 to indicate that motion control signals based on the newly calculated values for $\bar{P}_{EENEW}$ and $R_{EENEW}$ are to be sent to the slave computer 74. This causes the end effector 73 to assume a position and orientation determined by the current position and current orientation of the handle 102 when the alignment difference meets the second criterion.

Block 159 then directs the master apparatus 64 to copy the newly calculated end effector position vector $\bar{P}_{EENEW}$ ad end effector rotation matrix $R_{EENEW}$ into stores 147 and 149 of the previous buffer 141. The newly calculated end effector position vector $\bar{P}_{EENEW}$ and newly calculated end effector rotation matrix $R_{EENEW}$ are thus renamed as "previously calculated end effector position vector" $\bar{P}_{EEPREV}$ and "previously calculated end effector rotation matrix" $R_{EEPREV}$. By storing the newly calculated end effector position vector $\bar{P}_{EENEW}$ and newly calculated end effector rotation matrix $R_{EENEW}$, as previously calculated end effector position vector $\bar{P}_{EEPREV}$ and previously calculated end effector rotation matrix $R_{EEPREV}$, a subsequently acquired new end effector position vector $\bar{P}_{EENEW}$ and subsequently acquired new end effector rotation matrix $R_{EENEW}$ can be calculated from the next current handle position vector $\bar{P}_{MCURR}$ and next current handle position matrix $R_{MCURR}$.

If at block 208 the alignment difference meets the first criterion, i.e. alignment difference is not less than the threshold value but does not meet the second criterion, block 210 directs the master apparatus 64 to set the translation lock signal active to inform the feedback force control block (122 in FIG. 3) that it should cause the master apparatus 64 to send haptic feedback control signals to the control unit 92 to cause it to provide haptic feedback that impedes translational movement of the handle 102 while at the same time permitting rotational movement of the handle 102.

Figure 10:
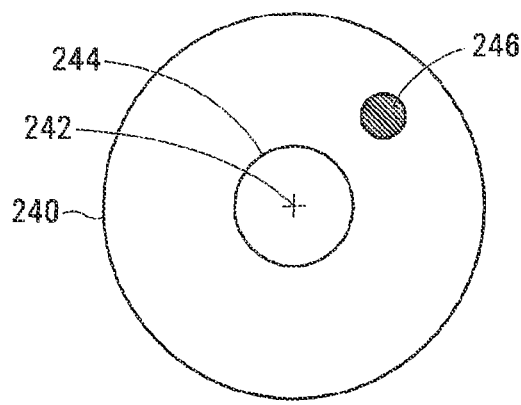
FIG. 10 is a schematic diagram of a visual representation of alignment difference between the input device and the end effector, for embodiments where alignment is defined as being when a single input device axis and a single end effector axis are coincident.
Figure 11:
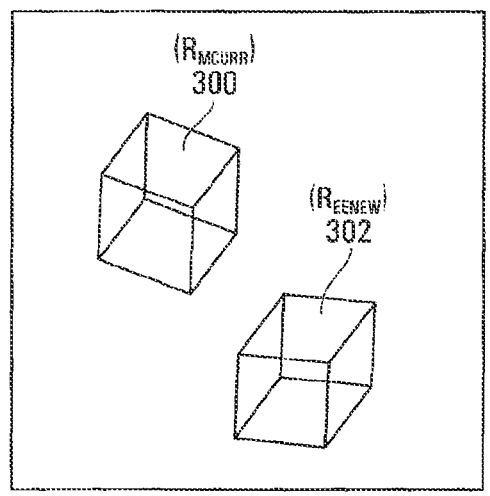
FIG. 11 is a schematic diagram of a visual representation of alignment difference between the input device and the end effector where alignment is defined as coincidence of all axes of the input device reference frame and end effector reference frame. i.e. frame $x_1$, $y_1$, $z_1$ coincident with $x_2$, $y_2$, $z_2$ in FIG. 7.

After executing block 210, the master apparatus 64 may be directed by an optional block, block 212, to start a program thread that directs the master apparatus 64 to produce annunciation signals for causing an annunciator to annunciate an indication of a relative alignment of the handle 102 and the end effector. The annunciator may include an audio producing device that changes a frequency of a signal in response to proximity of alignment and/or may include a display, possibly integrated into the viewer 62, for example, to provide a visual indication of the relative alignment between the end effector 73 and the handle 102. Such a visual presentation may be provided in the manner shown in FIG. 10, for example, for embodiments where alignment is defined as being when the z axes of the reference frames described by $R_{EENEW}$ and $R_{MCURR}$ are coincident. The visual representation includes a circular region 240, with an end effector marker 242 shown in a center thereof and a circular boundary 244 shown around the end effector marker to mark a boundary set by the alignment threshold value. The radius of the circular boundary 244 is larger when the alignment threshold is greater and smaller when the alignment threshold is smaller. The visual representation further includes a handle position representation 246 shown in a position depicting a distance and direction of the handle 102 relative to the end effector marker 242. The visual representation can be produced considering the z-axis of the end effector reference frame and the z-axis of the master handle reference frame. With the frame origins co-located at the center of the circular region 240 and the z-axis of the end effector pointing into the page normal to the page, a projection of the tip of the z axis of the master handle will appear as a dot in the circular region 240, the dot representing the handle position 246 and depicting a distance and direction of the misalignment relative to the z-axis of the end effector as depicted by the end effector marker at the center of the circular region 240. Other visual representations may alternatively be used. For example, referring to FIG. 11, in the case where alignment is defined as coincidence of the master reference frame and the end effector reference frame, two cubes 300 and 302 may be used to visually represent the orientation of the $R_{MCURR}$ reference frame associated with the handle 102 and the reference frame $R_{EENEW}$ associated with the end effector 73 respectively.

Referring back to FIGS. 8A-8B, after executing block 210 and, optionally, after initiating execution of the visual or audio representation thread with block 212, the master apparatus 64 is directed to block 163 causing it to set the "new" signal inactive to indicate to the motion control block 120 of FIG. 3 that it should send the slave control signals based on $\bar{P}_{EEPREV}$ and $R_{EEPREV}$. Thus, it will be appreciated that in the embodiment described, while the alignment difference remains equal to or greater than the alignment threshold, the master apparatus 64 executes blocks 210, 212, and 163 whereby, the user cannot effect translational movement of the handle 102 and can only rotate the handle until the handle is rotated into a position in which the alignment difference is less than the threshold value, at which point block 208 directs the master apparatus 64 to blocks 214, 215 and 159 which causes the master apparatus 64 to make the translation lock signal inactive, and to set the "new" signal active to indicate to the motion control block 120 that it should send the slave control signals based on $\bar{P}_{EENEW}$ and $R_{EENEW}$.

Referring back to FIG. 8A, at block 161, if the enablement signal is in the inactive state and while it remains in the inactive state, the master apparatus immediately executes block 163 of FIG. 8B which directs the master apparatus 64 to set the "new" signal inactive to indicate to the motion control block 120 in FIG. 3 that it should send the slave control signals based on the previously calculated values of $\bar{P}_{EEPREV}$ and $R_{EEPREV}$ in the eleventh and twelfth stores 147 and 149, respectively. The wire length signals produced by the motion control block 120 thus represent wire length values derived from the last saved values of $\bar{P}_{EEPREV}$ and $R_{EEPREV}$, causing the end effector 73 to remain stationary because the same motion control signals as were previously determined are sent to the slave computer 74. The end effector position and orientation calculation block 116 is then ended. As long as the enablement signal is inactive, motion control signals based only on the previously calculated end effector position and orientation signals are produced.

Accordingly, when the enablement signal is in the inactive state, the handle 102 can be moved and rotated and the calculations of $\bar{P}_{EENEW}$ and $R_{EENEW}$ will still be performed by block 160, but there will be no movement of the end effector 73, because the previous motion control signals are sent to the slave computer 74. This allows "clutching" or repositioning the handle 102 without corresponding movement of the end effector 73 and enables the end effector 73 to have increased range of movement when the end effector motion is constrained by the master controller workspace; for example, in the case where the scale factor "A" in the relation:

$$\bar{P}_{EENEW} = A(\bar{P}_{MCURR} - \bar{P}_{MBASE}) + \bar{P}_{EEBASE}$$

is such that the full range of motion in the master translational workspace does not cause the end effector to cover the full translational workspace of the slave instrument.

Referring back to FIG. 3, the feedback force control block 122 is running in the background and, in response to an active translation lock signal produced by the master apparatus 64 at block 210 of FIG. 8B, the feedback control block 122 directs the master apparatus 64 to produce haptic feedback force control signals for receipt by the control unit 92 that cause the control unit 92 to present a haptic force to the arms 94, 96, 98, to impede translational movement of the handle 102 and lock it in its current position in the handle translational workspace. In other words, the handle 102 is locked at its current position space by the haptic feedback produced by the control unit 92 in response to signals provided to it by the force control block 122. Rotational movement of the handle 102, can still be performed but translational movement cannot. The control unit 92 thus produces a constant handle position vector $\bar{P}_{MCURR}$ but produces a varying rotation matrix $R_{MCURR}$ dependent on the orientation of the handle 102.

When the translation lock signal is set inactive by block 214 of FIG. 8B by the end effector position and orientation calculation block 116, the feedback force control block 122 directs the master apparatus 64 to send haptic feedback control signals to the control unit 92 to cause the control unit to cease providing haptic force and the user can resume translating and rotating the handle 102 to any position within the handle translational workspace.

The motion control block 120 uses the configuration values produced by the kinematics block 118 to produce wire length values by applying transfer functions to the calculated configuration variables to determine required wire lengths. Such transfer functions can be derived theoretically and/or empirically, for example, for the specific tools used. The motion control block 120 is responsive to the "new" signal controlled by blocks 215 and 163 of FIG. 8B and causes the current wire length values to be represented by the slave control signals when the enablement signal is active and the alignment difference is less than the threshold and causes the previous wire length values to be represented by the slave control signals when the enablement signal is not active and when the enablement signal is active but the alignment difference is not less than the threshold.

Therefore, it can be seen that when the user releases the footswitch 170 such that the enablement signal transitions from inactive to active, the slave control signals produced $\bar{p}$ in response to actuation of the handle represent $\bar{P}_{EENEW}$ and $R_{EENEW}$ only if the alignment difference is less than the alignment threshold. Otherwise, if, when the enablement signal transitions from inactive to active, the alignment difference is not less than the alignment threshold, the previous wire length values are represented by the slave control signals.

In addition, when the alignment difference is not less than the alignment threshold, the handle is locked against translational movement and, optionally, the user is provided with a visual display of the relative alignment between the end effector 73 and the handle 102. In this state the user can only rotate the handle 102 until it is positioned into an orientation in which it is aligned with the end effector 73, within the bounds of the alignment threshold, at which time the newly calculated $\bar{P}_{EENEW}$ and $R_{EENEW}$ values are again represented in the control signals sent from the master apparatus 64 to the slave computer 74 to again provide for normal operation where the end effector 73 is positioned and rotated in response to positioning and rotation of the handle 102.

For example, referring to FIG. 7, the use could push the handle 102 in the $z_{mb}$ direction toward the control unit 92 while the enablement signal is active, whereby the end effector 73 is moved in the $z_{sb}$ direction corresponding to the movement of the handle 102. Then, the user can actuate the footswitch 170 to set the enablement signal inactive and while the footswitch is actuated, withdraw the handle 102 along the $z_{mb}$ axis in the opposite direction, away from the control unit 92. Since the motion control signals are produced based on the previously calculated end effector position $\bar{P}_{EEPREV}$ and the previously calculated end effector rotation $R_{EEPREV}$ when the footswitch is actuated, the end effector 73 remains stationary.

Then, the user can release the footswitch 170 to set the enablement signal active and, in response to the enablement signal transitioning from the "not active" state to the "active" state, block 216 of FIG. 6 directs the master apparatus 64 to store the current $\bar{p}$ values of the handle position $\bar{P}_{MCURR}$ and handle orientation $R_{MCURR}$ signals as new values of the master base position signals $\bar{P}_{MBASE}$ and new values of the master base orientation signals $R_{MBASE}$ respectively, and stores the newly calculated values of the end effector position signals $\bar{P}_{EENEW}$ and newly calculated values of the end effector 73 rotation signals $R_{EENEW}$ as new values of the end effector base position signals $\bar{P}_{EEBASE}$ and new values of the end effector base orientation signals $R_{EEBASE}$ respectively. Otherwise, upon release of the footswitch, the end effector 73 would "snap" to the absolute position directly determined by the position of the handle 102 and this could be dangerous if it were to occur inside a patient because the end effector 73 could tear into tissue or internal organs of the patient with possibly life-threatening effects. The user can then continue pushing the handle 102 in the $z_{mb}$ direction toward the control unit 92 while the end effector 73 is further moved in the $z_{sb}$ direction corresponding to the movement of the handle 102.

This provides a clutching effect which is achieved by causing movements of the handle 102 and movements of the end effector 73 to be made relative to the last-saved master base position ($\bar{P}_{MBASE}$) and rotation ($R_{MBASE}$) and the last saved end effector base position ($\bar{P}_{EEBASE}$) and rotation ($R_{EEBASE}$) respectively.

While the above described clutching effect is desirable to match the range of translational movement of the end effector 73 with the range of movement of the handle 102 and for the user to reposition their hands to a comfortable position for operation, it is not desirable for clutching to occur in rotation because this would cause a misalignment in orientation between the master and the slave, making the teleoperated slave difficult to control. In the absence of a mechanical means to maintain the orientation of the handle 102 it would be difficult for the user to rotate the handle 102 to cause it to be exactly aligned with the end effector 73 on release of the footswitch 170 so that normal operation can be resumed.

By locking the handles against translational movement when the alignment difference is not less than the threshold and by representing the previously calculated $\bar{P}_{EEPREV}$ and $R_{EEPREV}$ in the slave control signals, a safety feature is provided whereby translational movement of the handle is prevented and all movement of the end effector 73 is prevented until the handle 102 is generally rotationally aligned with the end effector 73.

While specific embodiments of the invention have been described and illustrated, such embodiments should be considered illustrative of the invention only and not as limiting the invention as construed in accordance with the accompanying claims.

The embodiments of the invention in which an exclusive property or privilege is claimed are defined as follows:

1. A non-transitory computer readable medium storing instructions that, when executed by a processor of a robotic surgery control system, cause the processor to:
    enable control of a handle in a first direction such that movement of the handle in the first direction controls corresponding movement of an end effector of a surgical tool in the first direction;
    determine an alignment difference between the handle and the end effector;
    in response to a determination that the alignment difference between the handle and the end effector does not satisfy an alignment threshold, disable control of movement of the end effector in a second direction by movement of the handle in the second direction; and
    in response to a determination that the alignment difference between the handle and the end effector satisfies the alignment threshold, enable control of the handle in the second direction such that movement of the handle in the second direction controls corresponding movement of the end effector in the second direction.

2. The medium of claim 1, wherein enabling control of the handle comprises enabling movement of the handle in the first direction.

3. The medium of claim 1, wherein enabling control of the handle in the second direction comprises enabling movement of the handle in the second direction.

4. The medium of claim 1, wherein the instructions, when executed by the processor, further cause the processor to:
in response to the determination that the alignment difference between the handle and the end effector does not satisfy the alignment threshold, disable movement of the end effector in the first direction responsive to movement of the handle in the first direction.

5. The medium of claim 1, wherein the instructions, when executed by the processor, further cause the processor to:
in response to the determination that the alignment difference between the handle and the end effector does not satisfy the alignment threshold, cause an end effector position and an end effector orientation to be determined based on a previous position and a previous orientation of the handle; and
in response to the determination that the alignment difference between the handle and the end effector satisfies the alignment threshold, cause the end effector position and the end effector orientation to be determined based on a current position and a current orientation of the handle.

6. A robotic surgery control system comprising:
an input configured to be moved in a first direction, wherein movement of the input in the first direction controls corresponding movement of an end effector of a surgical tool in the first direction; and
a processor configured to:
determine an alignment difference between the input and the end effector;
in response to a determination that the alignment difference does not satisfy an alignment threshold, disable control of movement of the end effector in the first direction by the input; and
in response to a determination that the alignment difference satisfies the alignment threshold, enable control of movement of the end effector in the first direction in response to corresponding movement of the input in the first direction.

7. The system of claim 6, wherein the input comprises a handle coupled to a control arm.

8. The system of claim 7, wherein the control arm is configured to provide movement of the input in the first direction and the handle is configured to provide movement of the input in a second direction, wherein the second direction is different than the first direction.

9. The system of claim 6, the input is further configured to be moved in a second direction, wherein movement of the input in the second direction controls corresponding movement of the end effector in the second direction.

10. The system of claim 9, wherein the processor is further configured to enable control of movement of the end effector in response to movement of the input.

11. The system of claim 10, wherein enabling control comprises enabling movement of the input in the second direction.

12. The system of claim 10, wherein enabling control comprises enabling movement of the input in the first direction.

13. The system of claim 10, wherein the processor is further configured to cause provision of an indication that control of movement in the first direction is disabled.

14. The system of claim 9, wherein the first direction is a translation direction and the second direction is rotational direction.

15. The system of claim 6, wherein the alignment difference comprises an alignment difference in a second direction in at least one degree of freedom in the second direction, and wherein the second direction is different than the first direction.

16. The system of claim 15, wherein the processor is further configured to determine the alignment difference based on a distance by which the end effector would have to be moved to become aligned with a current orientation of the input.

17. The system of claim 15, wherein the processor is further configured to:
determine a target orientation of the end effector based on a current orientation of the input; and
determine the alignment difference based on a difference between the current orientation of the input and the target orientation of the end effector.

18. The system of claim 6, wherein the processor is further configured to:
in response to the determination that the alignment difference does not satisfy the alignment threshold, disable control of movement of the end effector in a second direction by the input.

19. The system of claim 6, wherein the processor is further configured to:
in response to the determination that the alignment difference does not satisfy the alignment threshold, cause an end effector position and orientation to be determined based on a previous position and orientation of the input; and
in response to the determination that the alignment difference satisfies the alignment threshold, cause the end effector position and orientation to be determined based on a current position and orientation of the input.

* * * * *